US 6,693,286 B2

(12) United States Patent
Hasegawa et al.

(10) Patent No.: US 6,693,286 B2
(45) Date of Patent: Feb. 17, 2004

(54) METHOD FOR EVALUATING THE QUALITY OF A SEMICONDUCTOR SUBSTRATE

(75) Inventors: Takeshi Hasegawa, Saitama (JP); Terumi Ito, Saitama (JP); Hiroyuki Shiraki, Tokyo (JP)

(73) Assignee: Mitsubishi Materials Silicon Corporation, Tokyo (JP)

( * ) Notice: Subject to any disclaimer, the term of this patent is extended or adjusted under 35 U.S.C. 154(b) by 0 days.

(21) Appl. No.: 10/299,148

(22) Filed: Nov. 19, 2002

(65) Prior Publication Data
US 2003/0094579 A1 May 22, 2003

Related U.S. Application Data

(62) Division of application No. 09/815,208, filed on Mar. 22, 2001, now Pat. No. 6,534,774.

(30) Foreign Application Priority Data

Sep. 8, 2000 (JP) ........................................ 2000-272622
Sep. 8, 2000 (JP) ........................................ 2000-272623

(51) Int. Cl.$^7$ ................................................ G01N 21/64
(52) U.S. Cl. .................................. 250/458.1; 250/459.1
(58) Field of Search ........................ 250/458.1, 459.1, 250/438.7

(56) References Cited

U.S. PATENT DOCUMENTS

| 5,302,832 A | * | 4/1994 | Kitagawara et al. |
| 5,485,530 A | * | 1/1996 | Lakowicz et al. |
| 5,541,416 A | * | 7/1996 | Washizuka |
| 6,122,042 A | * | 9/2000 | Wunderman et al. |
| 6,157,037 A | * | 12/2000 | Danielson |
| 6,373,069 B1 | * | 4/2002 | Akaike et al. |

* cited by examiner

Primary Examiner—Albert Gagliaroi
(74) Attorney, Agent, or Firm—Reed Smith LLP

(57) ABSTRACT

A first chopper between a laser device and a semiconductor substrate chops an excitation light at a specific frequency, and a second chopper between the first chopper and the semiconductor substrate chops the excitation light at a variable frequency higher than the first chopper. A photoluminescence light emitted by the semiconductor substrate when the semiconductor substrate is intermittently irradiated with the excitation light is introduced into a monochromator. A controller obtains the decay time constant T of the photoluminescence light from variation of the average intensity of the photoluminescence light when gradually increasing the chopping frequency of the excitation light by controlling the second chopper, and computes the life time $\tau$ of the semiconductor substrate from an expression "$\tau=T/C$", where C is a constant. An object of the invention is to accurately evaluate impurities, defects and the like in a semiconductor substrate by obtaining quantitatively the life time of the semiconductor substrate having a long life time.

2 Claims, 4 Drawing Sheets

METHOD FOR EVALUATING THE QUALITY OF A SEMICONDUCTOR SUBSTRATE

CROSS-REFERENCE TO RELATED APPLICATIONS

This application is a divisional application of U.S. application Ser. No. 09/815,208, filed on Mar. 22, 2001, now U.S. Pat. No. 5,534,774 which claims the priority of Japanese Patent Application Nos. 2000-272622 and 2000-272623 both dated Sep. 8, 2000 the complete disclosures of which are hereby incorporated by reference.

BACKGROUND OF THE INVENTION

1. Field of the Invention

The present invention relates to a method and an apparatus for evaluating the quality of a semiconductor substrate represented by a silicon wafer such as an epitaxial wafer or the like, namely, for quantitatively evaluating impurities, defects and the like existing in a semiconductor substrate.

2. Description of the Related Art

Up to now, as an evaluation method of this kind, there has been disclosed a method for evaluating an epitaxial wafer used for a light emitting device, which method irradiates an epitaxial wafer for a light emitting device being a compound semiconductor with an excitation light, detects a photoluminescence light generated by excitation of carriers in an active layer of this wafer, and derives a non-radiative life time from a speed of variation in intensity of a photoluminescence light when the speed of variation in intensity of the photoluminescence light comes to be a fixed value (Japanese Patent Laid-Open Publication No. 2000-101,145).

In a method for evaluating an epitaxial wafer used for a light emitting device, composed in such a manner, since a non-radiative life time is a physical property value independent of an excited-carrier density, a good correlation with a luminous efficiency is kept with respect to a high-brightness LED having a high excited-carrier density. As the result, since it is possible to accurately and easily measure a non-radiative life time in an active layer without depending upon an excited-carrier density, it is possible to surely select an epitaxial wafer having a high luminous efficiency and improve the yield rate of manufacturing epitaxial wafers.

And there has been disclosed a method for evaluating a semiconductor device by measuring the decay time constant of a photoluminescence light on the basis of the photoluminescence light obtained by irradiating a semiconductor layer with a pulse light as applying a bias voltage in the forward direction between a p-type clad layer and an n-type clad layer, said semiconductor layer having a smaller band gap than the p-type clad layer and the n-type clad layer and being interposed between the p-type clad layer and the n-type clad layer (Japanese Patent Laid-Open Publication No. Hei 10-135,291 (1998/135,291)). This evaluation method computes the decay time constant of said photoluminescence light by subtracting the intensity of luminescence obtained by applying a bias voltage without irradiating an excitation light from the intensity of said photoluminescence light.

A semiconductor device evaluating method composed in such a manner is suitable for a semiconductor device having a pn junction, particularly a light emitting device such as an LED, a compound semiconductor laser and the like, and obtains the decay time constant of a photoluminescence light of a light emitting device by subtracting the intensity of a photoluminescence light reduced in influence of the inclination of an energy band of a semiconductor layer by applying a bias voltage in the forward direction to a pn junction without being irradiated with an excitation light from the intensity of a photoluminescence light when being irradiated with an excitation light. As the result, since even when the intensity of excitation varies, the inclination of an energy band and the decay time constant are little varied and the decay time constant can be measured more accurately, it is possible to improve the inspection of a light emitting device in accuracy and earlier detect the cause of a defect.

On the other hand, there has been disclosed a method for evaluating the life time of a semiconductor surface, said method evaluating the life time of a semiconductor thin layer or an area near it from the intensity of a light having a specific wavelength generated by recombination of electron-hole pairs generated near the surface of the semiconductor thin layer formed on the main surface of a semiconductor substrate by means of an excitation light having a larger energy than the band gap of the semiconductor to be inspected (Japanese Patent Laid-Open Publication No. Hei 8-139,146 (1996/139,146)); In this life time evaluating method, said light having a specific wavelength emitted by recombination of electron-hole pairs is a band-edge recombination and the area of depth in which electron-hole pairs are generated can be selectively changed by selection of the wavelength of said excitation light. And as its semiconductor substrate, a crystal of 0.1 Ωcm or less in resistivity is used in order to make the diffusion length of carriers comparatively short and the intensity of band-edge recombination stronger.

In a method for evaluating the life time of a semiconductor surface composed in such a way, since the area of depth in which electron-hole pairs are generated can be selectively changed by selecting the wavelength of an excitation light, it is possible to selectively evaluate only the life time of a semiconductor thin layer or the life times of both a semiconductor thin layer and a semiconductor substrate.

However, said existing method for evaluating an epitaxial wafer for a light emitting device disclosed in Japanese Patent Laid-Open Publication No. 2000-101,145 has a disadvantage that although a light emitting device is conceived to emit light in the irradiation domain of an excitation light due to a sufficiently short life time in the order of nanoseconds of an epitaxial wafer (compound semiconductor) used in the light emitting device, in a semiconductor substrate such as an indirect band gap silicon substrate or the like having a long life time in the order of microseconds, an accurate life time cannot be measured without considering the diffusion of carriers excited in a semiconductor substrate by irradiating it with an excitation light.

And said existing method for evaluating a semiconductor device disclosed in Japanese Patent Laid-Open Publication No.Hei 10-135,291 (1998/135,291) has a problem that since an object of measurement is a compound semiconductor having a double hetero-structure having a short decay time constant, although the decay time constant can be obtained with a comparative accuracy by applying a bias voltage in the forward direction to a pn junction and thereby reducing the influence of the inclination of an energy band of a semiconductor layer, in a semiconductor substrate such as an indirect band gap silicon substrate or the like having a long life time a decay time constant cannot be accurately measured without considering the diffusion of carriers excited in the semiconductor substrate.

Further, said existing method for evaluating the life time of a semiconductor surface disclosed in Japanese Patent Laid-Open Publication No.Hei 8-139,146(1996/139,146) has a disadvantage that a domain of depth in which electron-hole pairs are generated cannot be controlled even by changing the wavelength of an excitation light.

That is to say, electron-hole pairs generated in a semiconductor thin layer by being irradiated with an excitation light have a finite life time, they sometimes diffuse and recombine and thereby emit light outside the area irradiated with an excitation light. As the result, even when changing the wavelength of an excitation light, only the area irradiated with an excitation light does not necessarily emit light, and the domain of depth in which electron-hole pairs are generated cannot be controlled.

An object of the present invention is to provide a method and an apparatus for evaluating the quality of a semiconductor substrate, which can accurately evaluate impurities, defects and the like in a semiconductor substrate by obtaining quantitatively the life time of a semiconductor substrate having a long life time without breaking and touching the semiconductor substrate.

Another object of the present invention is to provide a method for evaluating the quality of a semiconductor substrate, which can obtain a photoluminescence light intensity having a positive correlation with the life time of a thin film layer or a bulk substrate and can accurately evaluate impurities, defects and the like in a thin film layer or a bulk substrate without breaking and touching the semiconductor substrate.

SUMMARY OF THE INVENTION

The inventors have thought that when a semiconductor substrate having a long life time of the order of several tens to several hundreds microseconds like a polished silicon substrate is used in measurement of the life time of a semiconductor substrate by a photoluminescence method, the decay of a photoluminescence light emitted from the semiconductor substrate cannot follow the chopping of an excitation light even if it is an ordinarily used chopping frequency of several tens to several hundreds Hz, and when the chopping frequency of an excitation light is gradually raised from a low frequency to a high frequency, said photoluminescence light is changed from an intermittent luminescence having a large fluctuation range to a luminescence having a small fluctuation range. The inventors have expected that the dependency upon the chopping frequency of a photoluminescence light varies according to the decay time constant of a photoluminescence light of each semiconductor substrate. In other words, the inventors have found that it is possible to obtain the decay time constant of a photoluminescence light on the basis of variation in the chopping frequency of an excitation light when the photoluminescence light changes from an intermittent luminescence to a continuous luminescence. Thereupon, the inventors have considered the transient response of a photoluminescence light and thus have come to attain the present invention of deriving a life time from the decay time constant of a photoluminescence light.

The first aspect of the present invention is a method for evaluating the quality of a semiconductor substrate, which method irradiates intermittently the surface of a semiconductor substrate with an excitation light, converts the intensity of a photoluminescence light emitted by the semiconductor substrate when it is intermittently irradiated with the excitation light into an electric signal, obtains the decay time constant T of the photoluminescence light from variation of the average intensity of the photoluminescence light converted into said electric signal by increasing gradually the chopping frequency of the excitation light, and computes a life time τ being an indicator of evaluation of the quality of a semiconductor substrate from an expression "τ=T/C", where C is a constant.

The method for evaluating the quality of a semiconductor substrate according to the first aspect of the present invention can obtain quantitatively the life time τ of a semiconductor substrate without breaking and touching the semiconductor substrate, and the obtained life time is a value representing quantitatively accurately impurities, defects and the like in the semiconductor substrate. And this quality evaluation method is suitable for obtaining the life time τ of a semiconductor substrate having a long life time.

The invention according to the second aspect of the present invention is an apparatus for evaluating the quality of a semiconductor substrate comprising;

a laser device for irradiating the surface of a semiconductor substrate with an excitation light, a first chopper being provided between the laser device and the semiconductor substrate, chopping the excitation light with which the semiconductor substrate is irradiated at a specified frequency, a second chopper being provided between the first chopper and the semiconductor substrate, being capable of chopping the excitation light at a variable frequency higher than the first chopper, a monochromator into which a photoluminescence light emitted by the semiconductor substrate when the semiconductor substrate is intermittently irradiated with the excitation light is introduced, a photodetector for converting the intensity of a photoluminescence light introduced into the monochromator into an electric signal, a lock-in amplifier for taking in and amplifying an electric signal converted by the photodetector and a pulse signal issued by the first chopper, and a controller for reading an electric signal and a pulse signal amplified by the lock-in amplifier, and changing the chopping frequency of the excitation light by controlling the second chopper, wherein;

said apparatus obtains the decay time constant T of the photoluminescence light from variation of the average intensity of the photoluminescence light converted into said electric signal when the controller increases gradually the chopping frequency of the excitation light by controlling the second chopper, and computes a life time τ being an indicator of evaluation of the semiconductor substrate from an expression (1).

$$\tau = T/C \tag{1},$$

where C is a constant.

The method for evaluating the quality of a semiconductor substrate according to the second aspect of the present invention, like the first aspect of the present invention, can obtain quantitatively the life time τ of a semiconductor substrate without breaking and touching the semiconductor substrate, and the obtained life time τ is a value representing quantitatively accurately impurities and defects in the semiconductor substrate. And this quality evaluation apparatus is suitable for obtaining the life time τ of a semiconductor substrate 11 having a long life time.

And when a coherent excitation light of a laser or the like is incident on the surface of a semiconductor substrate, this excitation light penetrates the substrate to a depth determined by an absorption coefficient corresponding to the excitation wavelength. This absorption coefficient is a value specific to a semiconductor material, and in case of inputting an excitation light emitted from an argon laser of 488 nm in wavelength into an epitaxial wafer composed of a silicon single crystal, the absorption coefficient is in the order of 1000 cm$^{-1}$ (kayser) and the depth of penetration is about 1 μm. And when a semiconductor substrate is irradiated with an excitation light, an electron and a hole excited by this excitation light, if there is not another recombination center, are recombined between a conduction band and a valence band to perform a band-edge recombination, and if there is a non-radiative center, excited carriers, are recombined in the non-radiative center to make weak the band-edge recombination.

For example, when an argon laser light of 488 nm in wavelength is made to be incident on the surface of an epitaxial layer (5 μm in thickness) of a p/p$^+$ epitaxial wafer, since its penetration depth is 1 μm, said laser light stops within the epitaxial layer of 5 μm in thickness. However, since a carrier has a finite life time in the epitaxial layer, the diffusion of carriers occurs and carriers diffuse to the bulk substrate side. As the result, when the life time of a wafer is short, carriers are difficult to penetrate the bulk substrate, and when the life time of a wafer is long, carriers are easy to penetrate the bulk substrate.

On the other hand, in case of evaluating only an epitaxial layer by means of a photoluminescence method, it is necessary to recognize the difference between a bulk substrate and an epitaxial layer. When the surface of a bulk substrate is irradiated with an excitation light, a photoluminescence light is emitted from the almost whole face in the thickness direction of the bulk substrate, but when the surface of an epitaxial layer of a p/p$^+$ epitaxial wafer is irradiated with an excitation light, since carriers diffuse, a photoluminescence light contains not only light emitted from the epitaxial layer (p) but also light emitted from the bulk substrate (p$^+$). Thereupon, the inventors have found a method for separating a photoluminescence light into a light emitted from the bulk substrate and a light emitted from the epitaxial layer in consideration of carrier diffusion and have come to achieved the present invention.

The invention according to the third aspect of the present invention is improvement of a method for evaluating the quality of a semiconductor substrate by intermittently irradiating the surface of a semiconductor substrate composed of a bulk substrate and a thin film layer deposited on this bulk substrate with an excitation light, making the semiconductor substrate emit a photoluminescence light when the semiconductor substrate is intermittently irradiated with the excitation light, and measuring the intensity of the photoluminescence light.

Its composition is characterized by;

obtaining the steady-state diffusion distribution of carriers generated in a thin film layer when it is irradiated with an excitation light by solving a diffusion equation, deriving an expression (2) for finding signal data [PL] of a photoluminescence-light intensity from said steady-state diffusion distribution of carriers, measuring the signal data of two kinds of photoluminescence light intensities by irradiating the surface of the semiconductor substrate with two kinds of excitation lights being different in incident intensity, and multiplying by a specified value the signal data being smaller in intensity out of two kinds of signal data of photoluminescence light intensities and thereafter subtracting the signal data being smaller in intensity from the signal data being larger in intensity, and thereby obtaining the signal data containing a more amount of light emitted from the thin film layer by eliminating the first term of said expression (2), or obtaining the signal data containing a more amount of light emitted from the bulk substrate by eliminating the second term of said expression (2).

$$\frac{[PL]}{CB_r} = p\tau \left[ 1 - \left(1 - \frac{p_b}{p}\sqrt{\frac{\tau_b}{\tau}}\right) e^{-\frac{d}{\sqrt{D\tau}}} \right] I + \frac{\tau^{3/2}}{2\sqrt{D}} \left[ 1 - \left(1 - \sqrt{\frac{\tau_b}{\tau}}\right) e^{-\frac{2d}{\sqrt{D\tau}}} \right] I^2$$
(2)

Where, [PL] is signal data of a photoluminescence light intensity, C is a constant, $B_r$ is a radiative recombination coefficient, p is a carrier density in a thin film layer, $p_b$ is a carrier density in a bulk substrate, τ is the life time of a carrier in the thin film layer, $τ_b$ is the life time of a carrier in the bulk substrate, D is a carrier diffusion coefficient, d is the thickness of the thin film layer, and I is the incident intensity of an excitation light.

The method for evaluating the quality of a semiconductor substrate according to the third aspect of the present invention can estimate the life time τ of a thin film layer having a positive correlation with a photoluminescence light intensity of the thin film layer, by eliminating the first term from the expression (2), without breaking and touching the semiconductor substrate, and the photoluminescence light intensity of the thin film layer comes to be a value representing accurately impurities and defects in the thin film layer. And this method can estimate the life time τ of a bulk substrate having a positive correlation with a photoluminescence light intensity of the bulk substrate by eliminating the second term from the expression (2), and the photoluminescence light intensity of the bulk substrate comes to be a value representing accurately impurities and defects in the bulk substrate. Further, this quality evaluation method is suitable for evaluation of the quality of an epitaxial layer of an epitaxial wafer or a bulk substrate.

DETAILED DESCRIPTION OF THE PREFERRED EMBODIMENTS

Next, a first embodiment of the present invention is described with reference to the drawings.

Figure 1:
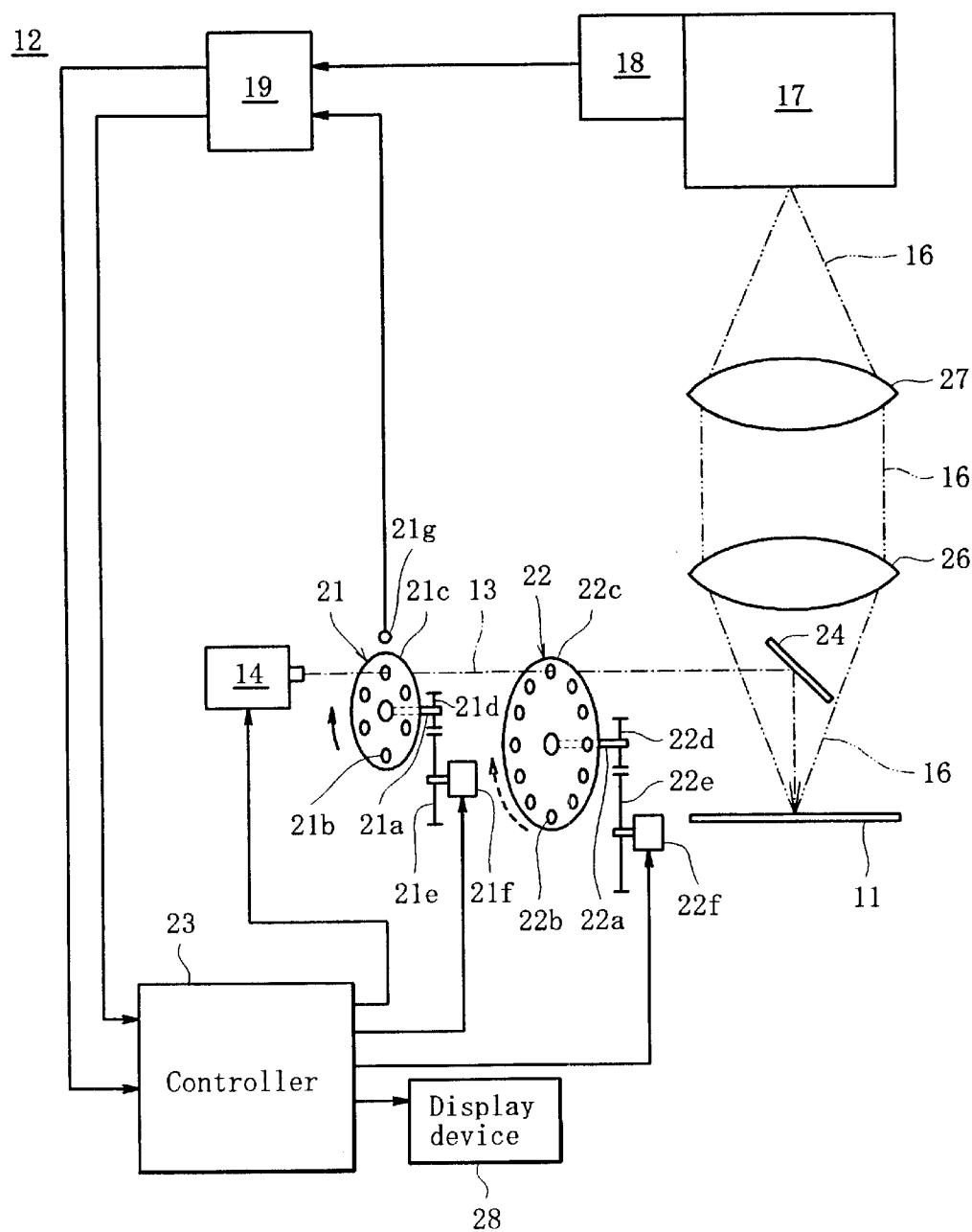
FIG. 1 is a composition diagram showing an apparatus for evaluating the quality of a semiconductor substrate of a first embodiment of the present invention.

As shown in FIG. 1, an apparatus 12 for evaluating the quality of a semiconductor substrate 11 comprises a laser device 14 for irradiating the surface of a semiconductor substrate 11 with an excitation light 13, a first chopper 21 provided between the laser device 14 and the semiconductor substrate 11, a second chopper 22 provided between the first chopper 21 and the semiconductor substrate 11, a monochromator 17 into which a photoluminescence light 16 emitted by the semiconductor substrate 11 when the excitation light 13 to be irradiated to the semiconductor substrate 11 is shut out is introduced, a photodetector 18 for converting the intensity of a photoluminescence light 16 introduced into the monochromator into an electric signal, a lock-in amplifier 19 for taking in and amplifying an electric signal converted by the photodetector, and a controller 23 for reading an electric signal amplified by the lock-in amplifier. As a semiconductor substrate 11, there are mentioned a polished silicon wafer having a long life time τ, an epitaxial wafer having an epitaxial thin film of a silicon single crystal grown on the surface of a mirror silicon wafer and the like, and as a laser device 14, there are mentioned a gas laser such as an argon laser or the like, a solid laser of YAG or the like, and a semiconductor laser of AlGaAs or the like.

The first chopper 21 has an opaque first disk 21c which turns around a first axis 21a and has a plurality of first small holes 21b formed on the circumference of a circle with the first axis as its center, a first driven gear 21d fixed on the first axis, a first driving gear 21e engaged with the first driven gear, and a first motor 21f for driving the first driving gear. An excitation light 13 can be chopped at a specified frequency by turning the first disk 21c at a specified speed of rotation by means of the first motor 21f and shutting out the excitation light 13 to be irradiated to the semiconductor substrate 11 with the first disk 21c or making the excitation light pass through the small holes 21b. And the first chopper 21 is provided with an oscillator 21g for generating a pulse signal having the same frequency as the chopping frequency of the excitation light 13 to be intermittently irradiated to the semiconductor substrate 11. The chopping frequency of the excitation light 13 by the chopper 21 is a specified frequency within a range of 0.5 to 10 Hz, preferably 4 to 6 Hz.

The second chopper 22 has an opaque second disk 22c which turns around a second axis 22a and has a plurality of second small holes 22b formed on the circumference of a circle with the second axis as its center, a second driven gear 22d fixed on the second axis, a second driving gear 22e engaged with the second driven gear, and a second motor 22f for driving the second driving gear. And the second disk 22c is made larger in diameter than the first disk 21c, and the second small holes 22b are made more in number than the first small holes 21b. An excitation light 13 can be chopped at a variable frequency being higher than the first chopper 21 by turning the second disk 22c at a variable rotation speed by the second motor 22f and shutting out the excitation light to be irradiated to the semiconductor substrate 11 with the second disk 22c or making the excitation light pass through the small holes 22b. The chopping frequency of the excitation light 13 by the chopper 22 is a variable frequency within a range of 50 to 4000 Hz. The reason why the range of variation of the chopping frequency of the excitation light 13 by the second chopper 22, being 50 to 4000 Hz, is made higher than the chopping frequency of the excitation light by the first chopper 21 is that a frequency of 4000 Hz is the upper limit in a mechanical chopper. However, it is possible in principle to measure a smaller decay time constant by using a high-frequency chopper.

And an excitation light 13 passing through the second small hole 22b of the second disk 22c is reflected by a collective mirror 24 and irradiated onto the surface of the semiconductor substrate 11. As the collective mirror 24, a concave mirror, a plane mirror or the like is used. In case of using a collective mirror 24 of a concave mirror of about 130 mm in focal length, the spot size (diameter) of an excitation area of the semiconductor substrate 11 is made to be about 0.5 mm, and in case of using a collective mirror 24 of a plane mirror being infinite in focal length, said spot size (diameter) is made to be about 1.5 mm.

The monochromator 17 has an entry slit for making a photoluminescence light 16 emitted by the semiconductor substrate 11 pass through, a grating for separating the photoluminescence light 16 passing through the entry slit into its spectral components, and an exit slit making the photoluminescence light separated by the grating pass through, although they are not illustrated. The grating has preferably 600 slits/mm. The photoluminescence light 16 emitted by the semiconductor substrate 11 is collected by two quartz lenses 26 and 27 being parallel with each other and then is introduced into the monochromator 17.

The lock-in amplifier 19 takes in and amplifies an electric signal converted by the photodetector 18 and a pulse signal issued by the oscillator 21g provided in the first chopper 21. And the control input of the controller 23 has an electric signal and a pulse signal amplified by said lock-in amplifier 19 inputted into it, and the control output of the controller 23 is connected to the laser device 14, the first motor 21f and the second motor 22f, and further a display device 23 such as a display, monitor and the like.

A method for evaluating the quality of a semiconductor substrate 11 using a quality evaluation apparatus 12 composed in such a manner is described.

First, the controller 23 turns on the laser device 14 and then rotates the first disk 21c at a specified rotation speed controlling the first motor 21f and further rotates the second disk 22c at a specified rotation speed controlling the second motor 22f, and irradiates intermittently the surface of a semiconductor substrate 11 with an excitation light 13. When the semiconductor substrate 11 is intermittently irradiated with the excitation light 13 and the irradiation of the excitation light 13 to the semiconductor substrate 11 is shut out, a photoluminescence light 16 emitted by the semiconductor substrate 11 passes through the two quartz lenses 26 and 27, and is separated by the monochromator 17. The intensity of this separated photoluminescence light 16 is converted into an electric signal by the photodetector 18 and this electric signal is amplified by the lock-in amplifier 19 together with a pulse signal issued by the oscillator 21g and inputted into the control input of the controller 23.

Next, when the controller 23 increases gradually said chopping frequency of the excitation light 13 by increasing gradually the rotation speed of the second disk 22c controlling the second motor 22f, the photoluminescence light 16 emitted by the semiconductor substrate 11 cannot follow the chopping frequency of the excitation light 13 and is changed from an intermittent luminescence light having a large fluctuation range to a luminescence light having a small fluctuation range. The controller 23 obtains the decay time constant T of the photoluminescence light 16 from variation of the average intensity of the photoluminescence light 16, namely, variation of the average intensity of the photoluminescence light 16 which is converted into an electric signal by the photodetector 18, amplified by the lock-in amplifier 19 and inputted into the control input of the controller 23. Further, the controller 23 computes from said decay time constant T a life time τ being an indicator of evaluation of the semiconductor substrate 11 using an expression (1);

$$\tau = T/C \tag{1},$$

and displays its value on a display device 28. A life time τ obtained in such a manner is a value representing quantitatively accurately impurities and defects in a semiconductor substrate 11, and such a method and an apparatus for evaluating the quality of a semiconductor substrate 11 are suitable for the life time τ of a semiconductor substrate 11 having a long life time τ such as a polished silicon substrate or the like.

The C of the above expression (1) is obtained by measuring the frequency response of a photoluminescence light 16 emitted from a semiconductor substrate 11 by chopping of an excitation light 13 and deriving an analytical solution of this frequency response and thereafter computing a decay time constant T by fitting the measurement result and analytical solution of said frequency response and measuring the life time τ of the semiconductor substrate 11 by means of a μ-PCD (microwave photoconductive decay) method, and comparing said decay time constant T with the life time τ. And the above C is a specific value within a range of 0.45 to 0.55. The reason why C is limited to a specific value within a range of 0.45 to 0.55 is that C is theoretically 0.5 but C is deviated due to an experimental error which occurs in measurement of the frequency response of said photoluminescence light 16 or in measurement of the life time τ by means of the μ-PCD method.

Figure 2:
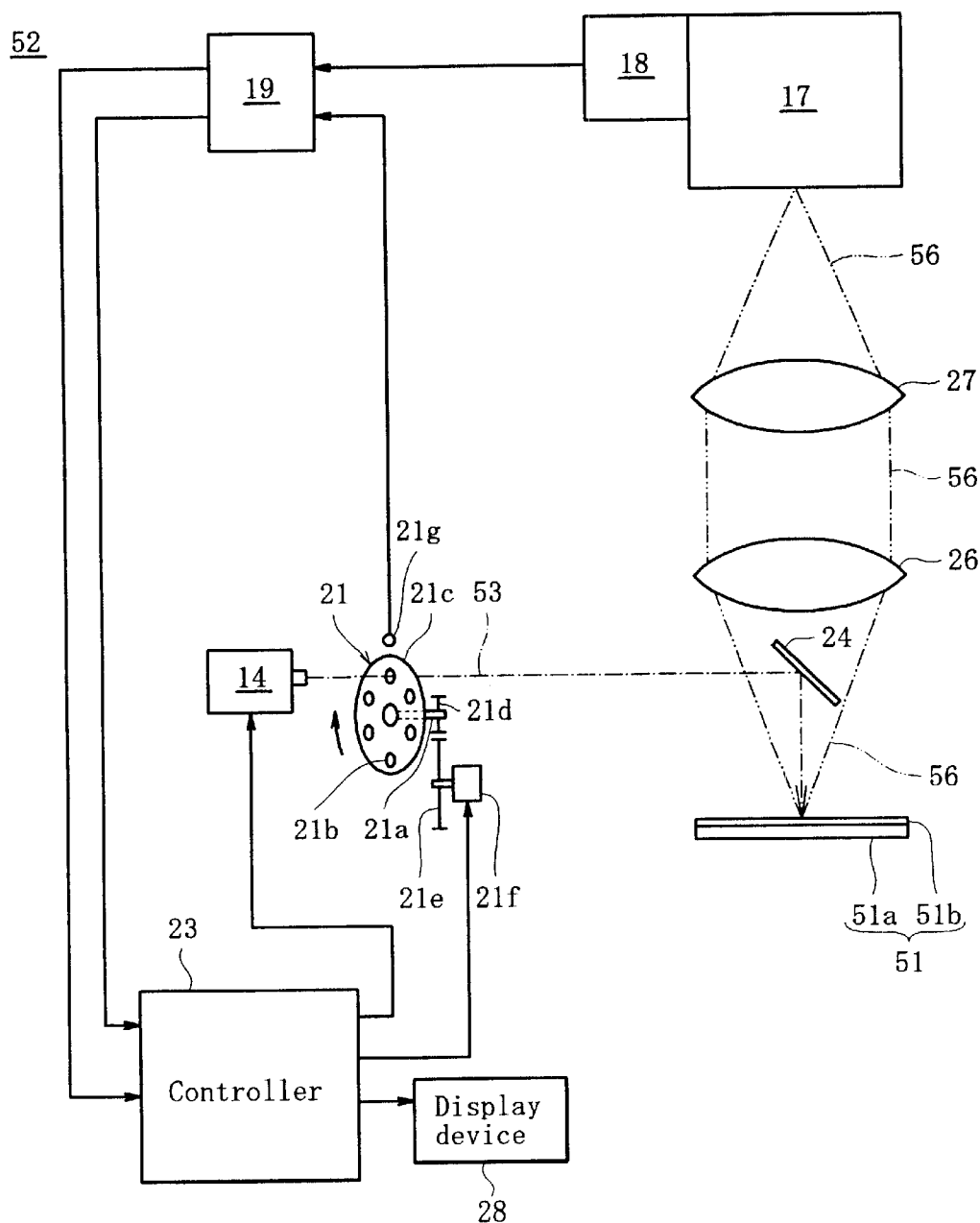
FIG. 2 is a composition diagram showing an apparatus for evaluating the quality of an epitaxial wafer of a second embodiment of the present invention.

FIG. 2 shows a second embodiment of the present invention. The same symbols of FIG. 2 as those of FIG. 1 show the same components as FIG. 1.

In this embodiment, a semiconductor substrate 51 is an epitaxial wafer having an epitaxial layer 51b deposited on the surface of a bulk substrate 51a. A quality evaluation apparatus 52 is used in order to evaluate the quality of this epitaxial wafer 51. This quality evaluation apparatus 52 comprises a laser device 14 for irradiating the surface of the wafer 51 with an excitation light 53, a first chopper 21 provided between the laser device and the wafer 51, a monochromator 17 into which a photoluminescence light 56 emitted by the wafer 51 when the wafer 51 is intermittently irradiated with the excitation light 53 is introduced, a photodetector 18 for converting the intensity of a photoluminescence light 56 introduced into this monochromator into an electric signal, a lock-in amplifier 19 for taking in and amplifying an electric signal converted by the photodetector, and a controller 23 for reading an electric signal amplified by the lock-in amplifier. That is to say, the quality evaluation apparatus 52 of this embodiment is made in the same way as the quality evaluation apparatus of the first embodiment except that the former does not have the second chopper in the latter.

As the laser device 14, a gas laser such as an argon laser or the like, a solid laser of YAG or the like, and a semiconductor laser of AlGaAs or the like which can change its incident intensity (photon number). The evaluation method of this embodiment can be applied also to a polished wafer (PW) having a DZ (denuded zone) in addition to an epitaxial wafer. In said polished wafer having a DZ, the DZ corresponds to an epitaxial layer. Further, the chopping frequency of an excitation light 53 by the first chopper 21 is a specific frequency within a range of 80 to 100 Hz, preferably 90 Hz.

A method for evaluating the quality of an epitaxial wafer 51 using a quality evaluation apparatus composed in such a manner is described.

First, this method obtains the steady-state diffusion distribution of carriers generated in a thin film layer 51b when it is irradiated with an excitation light 53 by solving a diffusion equation, and derives an expression (2) for finding signal data [PL] of a photoluminescence light intensity from said steady-state diffusion distribution of carriers.

$$\frac{[PL]}{CB_r} = p\tau\left[1-\left(1-\frac{p_b}{p}\sqrt{\frac{\tau_b}{\tau}}\right)e^{-\frac{d}{\sqrt{D\tau}}}\right]I + \frac{\tau^{3/2}}{2\sqrt{D}}\left[1-\left(1-\sqrt{\frac{\tau_b}{\tau}}\right)e^{-\frac{2d}{\sqrt{D\tau}}}\right]I^2 \quad (2)$$

Where, [PL] is signal data of a photoluminescence light intensity, C is a constant, $B_r$ is a radiative recombination coefficient, p is a carrier density in an epitaxial layer, $p_b$ is a carrier density in a bulk substrate, τ is the life time of a carrier in the epitaxial layer, $\tau_b$ is the life time of a carrier in the bulk substrate, D is a carrier diffusion coefficient, d is the thickness of the epitaxial layer, and I is the incident intensity of an excitation light.

Signal data [PL] of a photoluminescence light intensity of the above expression (2) consist of the first term being proportional to the incident intensity (photon number) I and the second term being proportional to the square of the incident intensity (photon number) I. And said first and second terms respectively contain both of luminescence lights emitted from the epitaxial layer and the bulk substrate. Comparing these terms in magnitude with each other, it has been found that a luminescence light emitted from the epitaxial layer is weaker than a luminescence light emitted from the bulk substrate, and there is a comparable difference between the luminescence light emitted from the epitaxial layer and the luminescence light emitted from the bulk substrate in the second term of expression (2). Thereupon, although signal data of a photoluminescence light intensity experimentally measured are the sum of a luminescence light emitted from the epitaxial layer and a luminescence light emitted from the bulk substrate, the first term of the above expression (2) can be eliminated by measuring two kinds of signal data of photoluminescence light intensities through irradiating the surface of the epitaxial wafer with two kinds of excitation lights being different in incident intensity, and multiplying by a specific value the signal data being smaller in intensity out of said two kinds of signal data of photoluminescence light intensities and thereafter subtracting the signal data being smaller in intensity from the signal data being larger in intensity.

Concretely, the controller 23 irradiates the epitaxial wafer with an excitation light having a specific incident intensity I (high), controlling the laser device 14. At this time the controller 23 rotates the first disk 21c at a specified rotation speed controlling the first motor 21f and irradiates intermittently the wafer 51 with an excitation light 53. A photoluminescence light 56 emitted by the wafer 51 when the wafer 51 is intermittently irradiated with the excitation light 53 and the irradiation of the excitation light 53 to the wafer 51 is shut out is separated by means of a monochromator 17 through two quartz lenses 26 and 27, is converted into an electric signal by a photodetector 18, and further is amplified by a lock-in amplifier 19 together with a pulse signal issued by an oscillator 21g. The signal data [PL] (high) of the amplified photoluminescence light intensity is displayed on a display device 28 as a map through the controller 23.

And the controller 23 controls the laser device 14 to irradiate the epitaxial wafer with an excitation light of such a weak incident intensity (low) so that said incident intensity I (high)=kI (low). It is assumed that the rotation speed of the first disk 21c at this time is the same as described above. In this state, in the same manner as described above, the signal data [PL] (low) of a photoluminescence light intensity is displayed as a map on the display device.

Further, this method obtains Δ[PL] by multiplying said [PL] (low) by k and subtracting k[PL] (low) from [PL] (high). That is to say, this method computes "Δ[PL]=[PL] (high)−k[PL] (low)" from expression (2). By this, the first term of expression (2) is eliminated and it is possible to obtain a map of signal data containing a more amount of light emitted from the epitaxial layer 51b. As the result, it is possible to estimate the life time τ of an epitaxial layer having a positive correlation with a photoluminescence light intensity of an epitaxial layer 51b without breaking and touching an epitaxial wafer 51, and this photoluminescence light intensity of the epitaxial layer comes to be a value representing accurately impurities and defects in the epitaxial layer.

Theoretically, when the thickness of an epitaxial layer becomes thicker, a map of signal data Δ[PL] of said photoluminescence light intensity comes to be a result of observing a more amount of light emitted from the epitaxial layer. For example, assuming that the thickness and resistivity of an epitaxial layer are 5 μm and 10 Ωcm, respectively, and the resistivity of a bulk substrate is 0.01 Ωcm, and the life times of the epitaxial layer and the bulk substrate are respectively 30 microseconds and 0.01 microsecond, a degree of 45% of the Δ[PL] is emitted as light from the epitaxial layer.

And it is acceptable also to irradiate the surface of a semiconductor substrate with two kinds of excitation lights being different in incident intensity, measure the signal data of said two kinds of photoluminescence light intensities, multiply by a specific value the signal data being smaller in intensity out of said two kinds of signal data of photoluminescence light intensities and thereafter subtract the signal data being smaller in intensity from the signal data being larger in intensity, and thereby eliminate the second term of said expression (2) and obtain the signal data containing a more amount of light emitted from the bulk substrate. By this, it is possible to obtain a photoluminescence light intensity having a positive correlation with the life time of a bulk substrate of a semiconductor substrate and this comes to be a value representing accurately impurities and defects in the bulk substrate. And this quality evaluation method is suitable for evaluation of the quality of a bulk substrate of an epitaxial wafer.

Embodiments

Next, embodiments of the present invention are described in detail.

Embodiment 1

Figure 3:
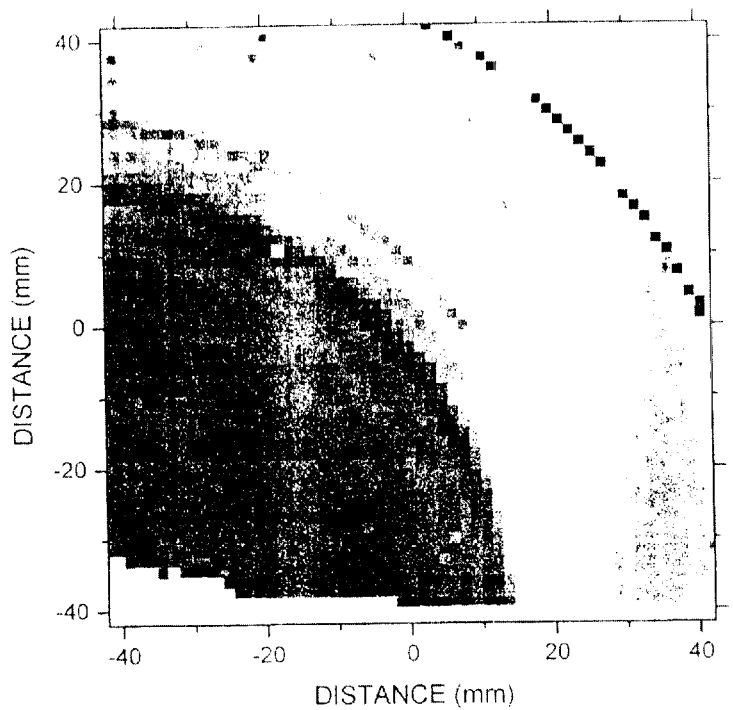
FIG. 3 shows a map of signal data of a photoluminescence light intensity [PL] (high) when the incident intensity of an excitation light is 40 mW.
Figure 4:
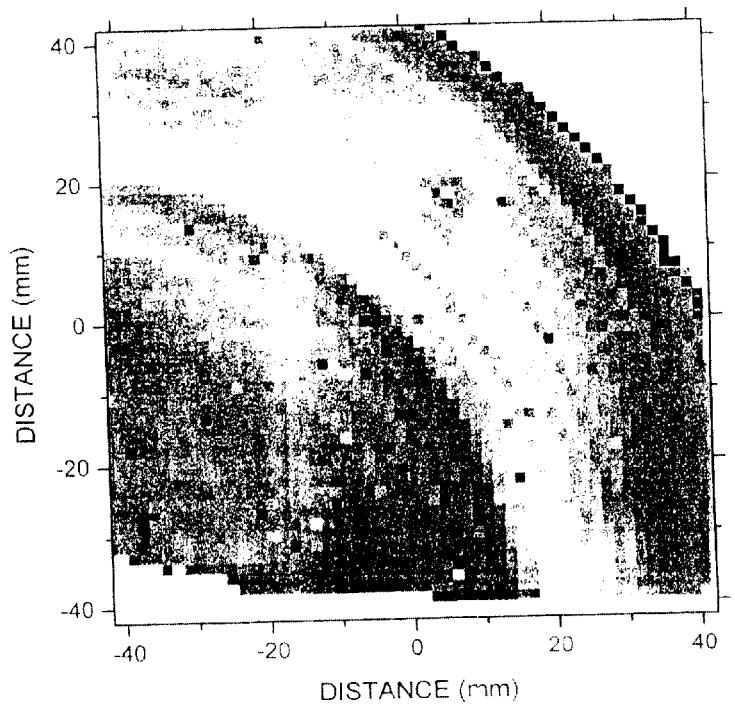
FIG. 4 shows a map of signal data of a photoluminescence light intensity [PL] (low) when the incident intensity of an excitation light is 8 mW.

This embodiment performed measurement of a map of signal data [PL] of a photoluminescence light intensity of a p/p⁺ epitaxial wafer 51 using an evaluation apparatus 52 shown in FIG. 2. A laser device 14 irradiated the surface of said wafer 51 with two kinds of excitation lights 53 of 40 mW and 8 mW being different in incident intensity. FIGS. 3 and 4 show signal data [PL] (high) and [PL] (low) of the photoluminescence light intensities at that time. FIG. 3 shows the case of 40 mW in incident intensity, and FIG. 4 shows the case of 8 mW in incident intensity. And a map of difference Δ[PL] ([PL] (high)−[PL] (low)) between the signal data of photoluminescence light intensities is made, and is shown in FIG. 5.

Figure 5:
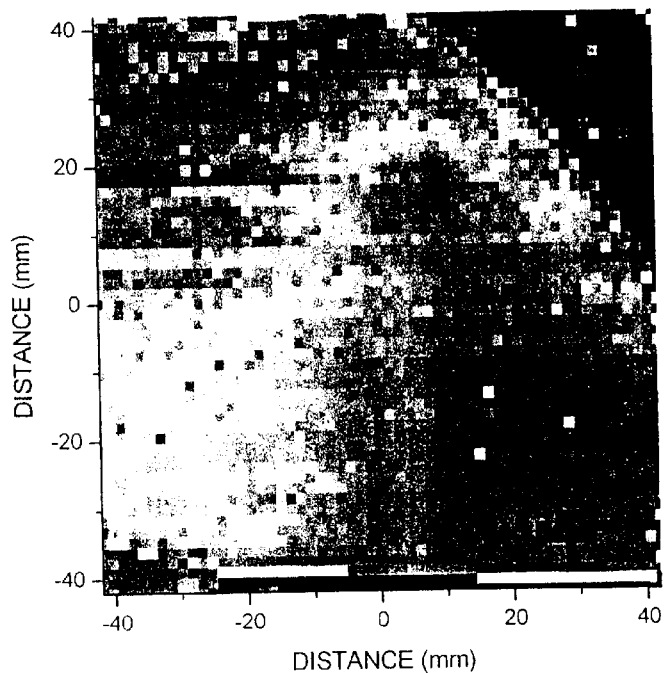
FIG. 5 shows a difference map of signal data of photoluminescence light intensities computed by subtracting k[PL] (low) from [PL] (high).

As apparently seen from FIGS. 3 and 4, although a pattern (striation) in the shape of concentric circles is seen with respect to a photoluminescence light 56 from the bulk substrate 51a, in FIG. 5 a pattern in the shape of concentric circles as described above disappears and a uniform map has been obtained. This map is expected to be a map containing a more amount of photoluminescence light 56 from the epitaxial layer 51b. A striped pattern laterally extending in the upper part of FIG. 5 has been generated due to fluctuation of the excitation light 53.

Embodiment 2

As shown in FIG. 1, this embodiment performed measurement of signal data [PL] of a photoluminescence light intensity of a polished wafer 11 using an evaluation apparatus 12. A laser device 14 irradiated the surface of said wafer 11 with an excitation light 13 of 488 nm in wavelength, 8 mW in incident intensity and 0.6 mm in irradiation spot diameter, said excitation light being chopped by a first chopper 21 and a second chopper 22. At this time, the chopping frequency of the excitation light 13 by the first chopper was set constant as 5 Hz. This was made in order to take this chopped signal into a lock-in amplifier 19 and use it as a reference signal. And the chopping frequency of the excitation light 13 by the second chopper 22 was made to be capable of varying within a range of 50 to 4000 Hz.

On the other hand, four kinds of wafers (samples A, B C and D) being respectively 740 microseconds, 330 microseconds, 30 microseconds and 16 microseconds in recombination life time τ measured by a μ-PCD method were used as polished wafers 11. This embodiment obtained a decay time constant T with respect to a chopping frequency by means of a controller 23. As the result, the decay time constant T of sample A was 340 microseconds, the decay time constant T of sample B was 150 microseconds, the decay time constant T of sample C was 13 microseconds, and the decay time constant T of sample D was 6.5 microseconds. The result is shown in FIG. 6.

Figure 6:
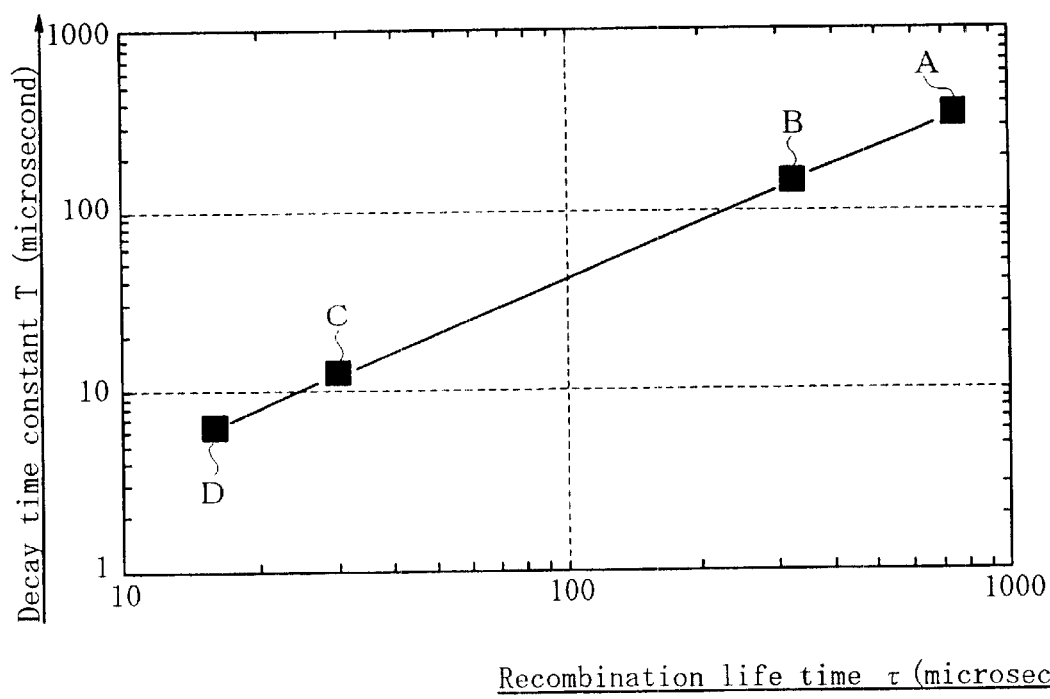
FIG. 6 is a diagram showing the relation between a recombination life time τ and a decay time constant T by obtaining the decay time constants T of wafers being different from one another in recombination life time τ.

As apparently seen from FIG. 6, it has been found that a decay time constant T is proportional to a life time τ, namely, it is possible to compute a life time τ by measuring a decay time constant T and substituting the value of this decay time constant T for T of expression (1).

As described above, since the present invention irradiates intermittently the surface of a semiconductor substrate with an excitation light, converts the intensity of a photoluminescence light emitted by the semiconductor substrate when the semiconductor substrate is intermittently irradiated with the excitation light into an electric signal, obtains the decay time constant T of the photoluminescence light from variation of the average intensity of the photoluminescence light converted into said electric signal as increasing gradually the chopping frequency of the excitation light, and computes a life time τ being an indicator of evaluation of the quality of the semiconductor substrate from an expression "τ=T/C", it is possible to obtain quantitatively the life time of a semiconductor substrate without breaking and touching the semiconductor substrate, and the obtained life time comes to be a value representing quantitatively accurately impurities and defects in the semiconductor substrate.

And this quality evaluation method is suitable for obtaining the life time of a semiconductor substrate having a long life time.

And in case that a first chopper between a laser device and a semiconductor substrate chops at a specific frequency an excitation light with which the semiconductor substrate is to be irradiated, a second chopper between the first chopper and the semiconductor substrate chops the excitation light at a variable frequency higher than the first chopper, and a controller obtains the decay time constant T of a photoluminescence light from variation of the average intensity of the photoluminescence light converted into an electric signal when gradually increasing the chopping frequency of the excitation light by controlling the second chopper and computes a life time τ being an evaluation criterion of a semiconductor substrate, it is possible to obtain quantitatively the life time of a semiconductor substrate without breaking and touching the semiconductor substrate, and the obtained life time comes to be a value representing quantitatively accurately impurities and defects in the semiconductor substrate. Additionally this quality evaluation method is suitable for obtaining the life time of a semiconductor substrate having a long life time.

And since the present invention obtains the steady-state diffusion distribution of carriers generated in a thin film layer when it is irradiated with an excitation light by solving a diffusion equation, derives an expression (2) for finding signal data of a photoluminescence light intensity from said steady-state diffusion distribution of carriers, measures signal data of said two kinds of photoluminescence light intensities by irradiating the surface of a semiconductor substrate with two kinds of excitation lights being different in incident intensity, multiplies by a specific value the signal data being smaller in intensity out of said two kinds of signal data of photoluminescence light intensities and thereafter subtracts the signal data being smaller in intensity from the signal data being larger in intensity, and thereby obtains the signal data containing a more amount of light emitted from the thin film layer by eliminating the first term of said expression (2) or obtains the signal data containing a more amount of light emitted from the bulk substrate by eliminating the second term of said expression (2), it is possible to obtain the photoluminescence light intensity of the thin film layer or the bulk substrate having a positive correlation with the life time of the thin film layer or the bulk substrate without breaking and touching the semiconductor substrate, and the obtained photoluminescence light intensity comes to be a value representing accurately impurities and defects in the thin film layer or the bulk substrate.

And this quality evaluation method is suitable for evaluation of the quality of an epitaxial layer or a bulk substrate of an epitaxial wafer.

Furthermore, in comparison with an existing method for evaluating the life time of a semiconductor surface which method needs to limit the resistivity of a semiconductor substrate to a crystal of 0.1 Ωcm or less in order to make comparatively short the depth of diffusion of carriers and make stronger the intensity of band-edge recombination, a method for evaluating the quality of a semiconductor substrate of the present invention can be applied not only to a wafer of 0.1 Ωcm or less in resistivity but also to a semiconductor substrate being more than 0.1 Ωcm in resistivity.

What is claimed is:

1. A method for evaluating the quality of a semiconductor substrate by irradiating intermittently the surface of a semiconductor substrate composed of a bulk substrate and a thin film layer deposited on said bulk substrate with an excitation light, making said semiconductor substrate emit a photoluminescence light when said semiconductor substrate is intermittently irradiated with said excitation light, and measuring the intensity of said photoluminescence light, said method comprising the steps of;

obtaining the steady-state diffusion distribution of carriers generated in said thin film layer when said thin film layer is irradiated with said excitation light by solving a diffusion equation, deriving an expression (2) for finding signal data of a photoluminescence light intensity from said steady-state diffusion distribution of carriers, measuring signal data of two kinds of photoluminescence light intensities by irradiating the surface of said semiconductor substrate with two kinds of excitation lights being different in incident intensity, and multiplying by a specific value the signal data being smaller in intensity out of said two kinds of signal data of photoluminescence light intensities and thereafter subtracting the signal data being smaller in intensity from the signal data being larger in intensity, and thereby obtaining the signal data containing a more amount of light emitted from the thin film layer by eliminating the first term of said expression (2), or obtaining the signal data containing a more amount of light emitted from the bulk substrate by eliminating the second term of said expression (2):

$$\frac{[PL]}{CB_r} = p\tau \left[ 1 - \left( 1 - \frac{p_b}{p} \sqrt{\frac{\tau_b}{\tau}} \right) e^{-\frac{d}{\sqrt{D\tau}}} \right] I + \frac{\tau^{3/2}}{2\sqrt{D}} \left[ 1 - \left( 1 - \sqrt{\frac{\tau_b}{\tau}} \right) e^{-\frac{2d}{\sqrt{D\tau}}} \right] I^2, \quad (2)$$

where [PL] is signal data of a photoluminescence light intensity,

C is a constant, $B_r$ is a radiative recombination coefficient, p is a carrier density in a thin film layer, $p_b$ is a carrier density in a bulk substrate, τ is the life time of a carrier in the thin film layer, $\tau_b$ is the life time of a carrier in the bulk substrate, D is a carrier diffusion coefficient, d is the thickness of the thin film layer, and I is the incident intensity of an excitation light.

2. A method for evaluating the quality of a semiconductor substrate according to claim 1, wherein;

said thin film layer is an epitaxial layer or a denuded zone.

* * * * *